(12) United States Patent
Doi et al.

(10) Patent No.: US 9,822,922 B2
(45) Date of Patent: Nov. 21, 2017

(54) MEDICAL STAND APPARATUS

(71) Applicant: MITAKA KOHKI CO., LTD., Tokyo (JP)

(72) Inventors: Masao Doi, Tokyo (JP); Katsuyuki Nakamura, Tokyo (JP)

(73) Assignee: MITAKA KOHKI CO., LTD., Tokyo (JP)

( * ) Notice: Subject to any disclaimer, the term of this patent is extended or adjusted under 35 U.S.C. 154(b) by 0 days.

(21) Appl. No.: 15/077,121

(22) Filed: Mar. 22, 2016

(65) Prior Publication Data
US 2016/0281911 A1    Sep. 29, 2016

(30) Foreign Application Priority Data
Mar. 24, 2015    (JP) ................................ 2015-060495

(51) Int. Cl.
| | | |
|---|---|---|
| A47F 5/00 | (2006.01) | |
| F16M 11/20 | (2006.01) | |
| F16M 11/22 | (2006.01) | |
| A61B 90/25 | (2016.01) | |

(52) U.S. Cl.
CPC ......... *F16M 11/2021* (2013.01); *A61B 90/25* (2016.02); *F16M 11/22* (2013.01); *F16M 2200/063* (2013.01); *F16M 2200/068* (2013.01)

(58) Field of Classification Search
CPC ............... F16M 11/2021; F16M 11/22; F16M 2200/063; F16M 2200/068; A61B 90/25; A61B 46/10; A61B 19/081

USPC ................. 248/125.1, 125.2, 123.2, 123.11; 359/384
See application file for complete search history.

(56) References Cited

U.S. PATENT DOCUMENTS

| | | | | |
|---|---|---|---|---|
| 5,825,536 | A | * 10/1998 | Yasunaga | A61B 90/25 248/123.11 |
| 6,050,530 | A | * 4/2000 | Nakamura | A61B 50/28 248/123.2 |
| 7,472,872 | B2 | * 1/2009 | Nakamura | F16M 11/105 248/123.2 |
| 9,563,045 | B2 | * 2/2017 | Doi | G02B 21/0012 |
| 2008/0083856 | A1 | * 4/2008 | Nakamura | G02B 7/001 248/125.2 |
| 2014/0055850 | A1 | * 2/2014 | Doi | G02B 21/0012 359/384 |

FOREIGN PATENT DOCUMENTS

| | | |
|---|---|---|
| JP | 4480703 | 6/2010 |
| JP | 2014-39644 | 3/2014 |

\* cited by examiner

*Primary Examiner* — Todd M Epps
(74) *Attorney, Agent, or Firm* — Greenblum & Bernstein, P.L.C.

(57) ABSTRACT

A medical stand apparatus includes a cylindrical lower arm that accommodates an upper arm divided into sections, so that only the lower arm is visible from the outside and so that a drape can tightly be fastened to the lower arm. The upper arm sections are connected to each other through a shaft that is guided along an arc groove of a bracket. This configuration is beneficial to reduce a diameter of the lower arm when the upper and lower arms are curved.

6 Claims, 5 Drawing Sheets

MEDICAL STAND APPARATUS

BACKGROUND OF THE INVENTION

1. Field of the Invention

The present invention relates to a medical stand apparatus.

2. Description of Related Art

A medical stand apparatus is set on a floor or ceiling in an operating room and supports a medical unit such as a surgical microscope, a camera, or the like so that the medical unit is movable to an optional position. The medical stand apparatus employs parallel linkages to move the medical unit in any of front, rear, up, and down directions while keeping the position of the medical unit such as vertical.

Among the parallel linkages arranged in the medical stand apparatus, one used to move the medical unit upward and downward includes a base arm arranged on the medical stand apparatus, a front arm supporting the medical unit, and upper and lower arms connecting the base and front arms to each other. The base arm is stationary and the front arm is moved upward and downward together with the medical unit. During the movement, the front arm that is supporting the medical unit is kept vertical by the parallel linkage, and therefore, an observer is able to easily observe or photograph an objective area with the medical unit.

The upper and lower arms of the parallel linkage, the medical unit, and the like on the medical stand apparatus are covered with a drape to secure an aseptic condition. The drape must not sag to block the sight of an observer, and therefore, is fastened to the upper and lower arms of the parallel linkage with bands.

Related arts concerning the medical stand apparatus are disclosed in, for example, Japanese Patent No. 4480703 and Japanese Unexamined Patent Application Publication No. 2014-39644.

SUMMARY OF THE INVENTION

According to the related arts, the upper and lower arms of the parallel linkage move relative to each other when the medical unit is moved upward or downward. To permit such relative movement of the upper and lower arms, the related arts loosely fasten the drape to the upper and lower arms when covering them with the drape. Namely, the related arts are unable to tightly fasten the drape to the upper and lower arms.

In consideration of the problems of the related arts, the present invention provides a medical stand apparatus that allows a drape to be tightly fastened to upper and lower arms of a parallel linkage that supports a medical unit.

According to an aspect of the present invention, the medial steno apparatus includes a vertical base arm arranged on the apparatus, a vertical front arm supporting a medical unit at lower part of the front arm, and upper and lower arms that are structurally parallel with each other and connect upper and lower ends of the base and front arms to each other to form a parallel linkage that allows the front arm with the medical unit to keep a vertical state and to move upward and downward around the base arm. The lower arm is a cylindrical member that accommodates the upper arm therein.

According to another aspect of the present invention, the medical stand apparatus includes a base arm arranged on the apparatus and having a first end to which a first end of a lower arm is rotatably connected, an arc groove mechanism having a predetermined length of radius around a virtual center that is positionally fixed to intermediate part of the lower arm, and a first sub-link whose first end is rotatably connected through a shaft to a second end of the base arm, the second end of the base arm being distanced from the first end thereof by the predetermined length, a second end of the first link being movably supported in an arc groove of the arc groove mechanism, the first sub-link, lower arm, and base arm serving as links to form a first horizontal parallel sub-linkage.

The apparatus further includes a second sub-link whose first end is connected to the second end of the first sub-link and is movably supported in the arc groove and a vertical sub-link whose second end is connected through a shaft to a second end of the second sub-link, a first end of the vertical sub-link being distanced from the second end thereof by the predetermined length and being connected to a second end of the lower arm, the vertical sub-link supporting a load, the second sub-link, lower arm, and vertical sub-link serving as links to form a second horizontal parallel sub-linkage. The first and second horizontal parallel sub-linkages allow the vertical sub-link to keep a vertical 1 state and to move upward and downward around the base arm.

DESCRIPTION OF PREFERRED EMBODIMENTS

Figure 1:
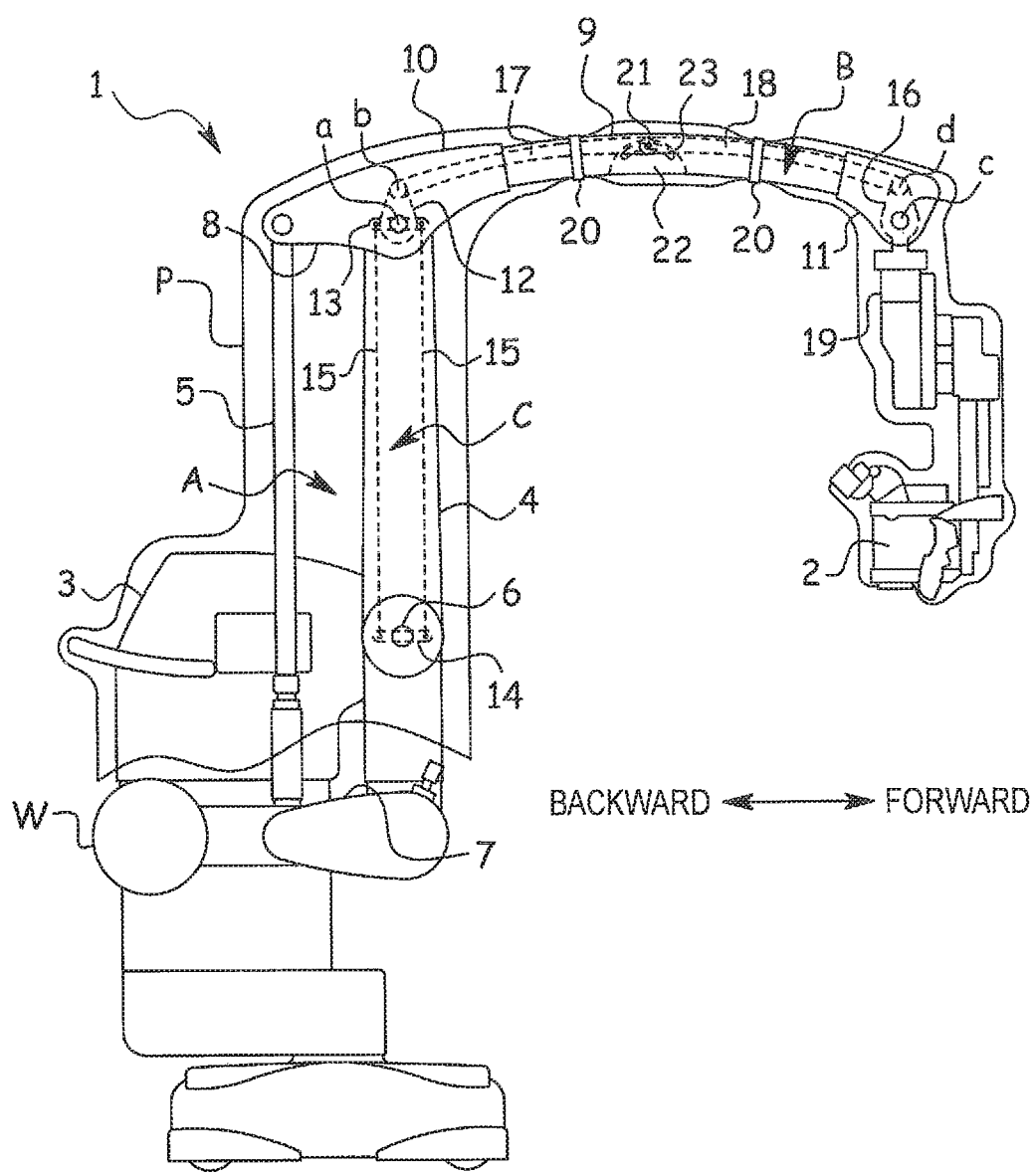
FIG. 1 is a general view illustrating a medical stand apparatus according to an embodiment of the present invention.

A medical stand apparatus according to an embodiment of the present invention will be explained with reference to FIGS. 1 to 9.

The medical stand apparatus 1 is set in an operating room and supports a medical unit such as a surgical microscope 2. The apparatus 1 includes a stand body 3 and a first parallel linkage A. The first parallel linkage A extends longitudinally/vertically, includes a front arm 4 and a rear arm 5, and is tiltable frontward and rearward around a rotary shaft 6 that is arranged at intermediate part of the front arm 4.

The first parallel linkage A includes a bottom arm 7 extending rearward to support a counterweight W. Opposite to the bottom arm 7, the linkage A includes a top arm 8 extending forward to serve as a lower arm 9. The lower arm 9 is a link of a second parallel linkage B that extends horizontally/laterally.

The lower arm 9 is made of metal, is cylindrical, and is curved upward to secure a work space under the lower arm 9. Ends of the lower arm 9 are closed with hollow members 10 and 11, which are parts of the lower arm 9. Part of the hollow member 10 behind the front arm 4 serves as the top arm 8.

An upper end of the front arm 4 is supported with a shaft that supports a lower end "a" of a base arm 12 of the second parallel linkage B. The base arm 12 is arranged inside the lower arm 9 and integrally has at the lower end "a" a horizontal lever 13. Another horizontal lever 14 is fixed to the stand body 3 at the rotary shaft 6 of the front arm 4. Ends of the horizontal levers 13 and 14 are connected to each other with parallel vertical sub-arms 15, thereby forming a third parallel linkage C. This linkage C maintains the base arm 12 of the second parallel linkage B in a vertical state when the first parallel linkage A including the front arm 4 tilts.

Inside the front hollow member 11 of the lower arm 9, a lower end "c" of a front arm 16 of the second parallel linkage B is supported with a shaft. The front arm 16 is similar to the base arm 12. Upper ends "b" and "d" of the base and front arms 12 and 16 are connected to each other with an upper arm 17-18 within the lower arm 9, thereby forming the second parallel linkage B. The upper arm 17-18 is made of upper arm sections 17 and 18. Similar to the lower arm 9, the upper arm 17-18 is curved upward.

The lower end "c" of the front arm 16 integrally has a hanging arm 19 extending downward. A lower end of the hanging arm 19 supports the surgical microscope 2.

The medical stand apparatus 1 including the surgical microscope 2 is covered with a drape P to secure an aseptic state. Part of the drape P that covers the lower arm 9 must not block the sight of an operator, and therefore, is tightly fastened to the lower arm 9 with bands 20.

The second parallel linkage B is configured by two parallel sub-linkages B1 and B2 that are connected to each other with predetermined restrictive conditions.

The upper arm sections 17 and 18 that form the upper arm 17-18 are connected to each other with a horizontal connection shaft 21 that is supported with a bracket 22. The bracket 22 has an erect U-shaped cross section and is fixed to meddle part of an inner bottom face of the cylindrical lower arm 9. Each side wall of the bracket 22 has an arc groove 23 to receive ends of the connection shaft 21. The connection shaft 21 moves along the arc groove 23 while being restricted by the arc groove 23. Part of the cylindrical lower arm 9 has an opening (not illustrated) that is opened and closed when installing the bracket 22 in the lower arm 9.

A curvature of the arc groove 2 is equal to the curvature of each of arcs along which the upper ends "b" and "d" of the base and front arms 12 and 16 move around the lower ends "a" and "c" thereof, respectively. Namely, a circle R along which the upper end "b" moves around the lower end "a" of the base arm 12, a circle R along which the upper end "d" moves around the lower end "c" of the front arm 16, and 4 circle. R along which the arc groove 23 is formed have an equal radius or curvature.

According to the present embodiment, the second parallel linkage B is formed by connecting the first and second horizontal/lateral parallel sub-linkages 31 and B2 to each other. Namely, the sub-linkages 31 and 32 are arranged side by side and adjacent vertical links of the sub-linkages 31 and 32 are joined together with restrictive conditions. More precisely, the first sub-linkage B1 is formed with the upper arm section 17 serving as a first horizontal link, the lower arm 9 serving as a second horizontal link a-VC, a first vertical link a-b (the base arm 12) having a length R, and a second vertical link VC-21 having the length R.

The second sub-linkage B2 is formed with the upper arm section 18 serving as a third horizontal link, the lower arm 9 serving as a fourth horizontal link VC-c, a third vertical link VC-21 having the length R, and a fourth vertical link c-d (the front arm 16) having the length R.

The second vertical link VC-21 of the first sub-linkage B1 and the third vertical link VC-21 of the second sub-linkage B2 jointly form a common vertical link VC-21. A rotary axis at an end of the common vertical link VC-21 is supported at a virtual center VC that is positionally fixed to the lower arm 9, and therefore, the rotary shaft 21 at the other end of the common vertical rink VC-21 is movable around the virtual center VC along the arc groove 23. Accordingly, the first vertical link a-b, fourth vertical link c-d, and common vertical link VC-21 having the same length R are always kept parallel with one another.

To realize the same restrictive conditions as those realized with an actual common vertical link VC-21, the present embodiment employs the arc groove mechanism including the bracket 22 and arc groove 23 having the radius R around the virtual center VC and fixes the arc groove mechanism to an intermediate position of the lower arm 9 between the lower ends "a" and "c" of the base and front arms 12 and 16. With this, the present embodiment eliminates the actual common vertical link VC-21 and an actual rotary axis at the virtual center VC. In this way, the first and second horizontal parallel sub-linkages B1 and B2 are connected to each other to form the second parallel linkage B that maintains a vertical parallel relationship between the first vertical link a-b (the base arm 12) and the fourth vertical link c-d (the front arm 16).

Figure 3:
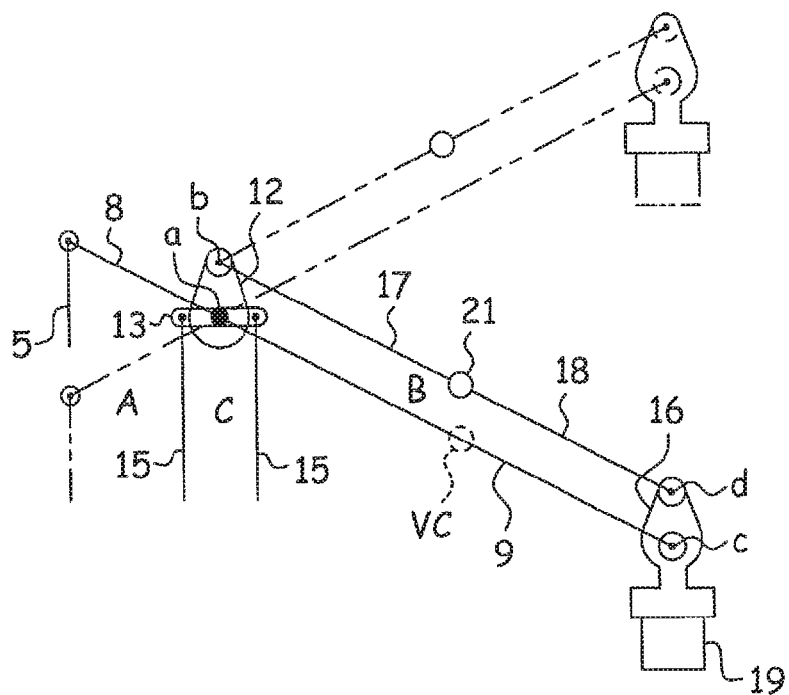
FIG. 3 is a view illustrating a mechanism of the parallel linkage.

The virtual center VP is on a virtual line passing through the rotation shafts at the ends "a" and "c" of the base and front arms 2 and 16 as illustrated in FIG. 3. No rotation shaft is actually needed at the virtual center VC, and therefore, the actual lower arm 9 can be formed into any shape. The arc groove 23, i.e., the bracket 22 is fixed to the lower arm 9, and therefore, the second parallel linkage B operates as if the common vertical link VC-21 is actually arranged between the rotation shaft 21 and the virtual rotation axis positioned at the virtual center VC.

The second horizontal link a-VC and fourth horizontal link VC-c form a predetermined angle relative to each other, are fixed to each other, and are integral with the lower arm 9. Accordingly, the lower arm 9 and first parallel linkage A are able to secure a weight balance (torque balance) between the surgical microscope and the counterweight W.

A height position of the surgical microscope 2 is changeable by moving the front arm 16 side of the lower arm 9 upward or downward. At this time, the front arm 16 is kept vertical and the positions of the upper arm 17-18, lower arm 9 (bracket 22), and front arm 16 change relative to one another.

Figure 8:
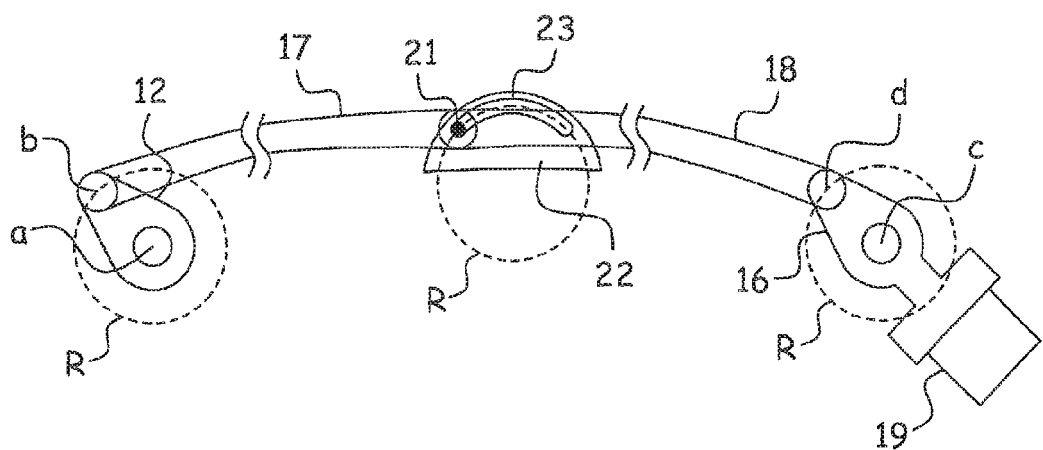
FIG. 8 is an enlarged side view illustrating the upper arm moved downward, base and front arms (12, 16) of the parallel linkage being tilted in FIG. 8 to make bracket (22) horizontal corresponding to FIG. 7.
Figure 9:
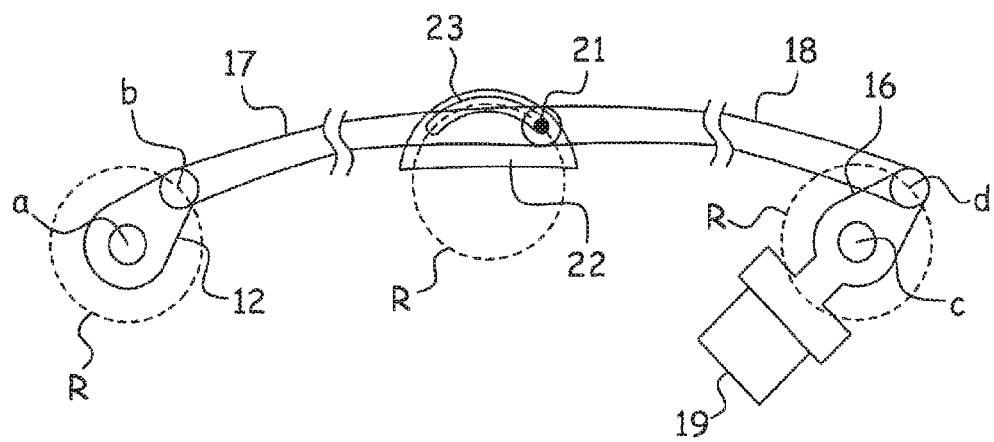
FIG. 9 is an enlarged side view illustrating the upper arm moved upward, the base and front arms of the parallel linkage being tilted in FIG. 9 to make the bracket horizontal corresponding to FIG. 7.

FIGS. 8 and 9 illustrate the relative positions of the upper arm 17-18, lower arm 9 (bracket 22), and front arm 16 when the front arm 16, i.e., the surgical microscope 2 is moved downward (FIG. 8) and upward (FIG. 9). In FIGS. 8 and 9, the bracket 22 is illustrated as horizontal to clarify the relative positions of the arms, although the bracket 22 tilts and the front arm 16 has always the same position on such as vertical or plumb in practice. As illustrated, the position of the upper arm. 17-18 changes in front and rear directions with respect to the bracket 22, to change angles of the base and front arms 12 and 16 at the ends of the upper arm 17-18. At this time, the upper ends "b" and "d" of the base and front arms 12 and 16 and the connection shaft 21 connecting the upper arm sections 17 and 18 to each other move along arc loci that are identical to one another to maintain the function of the second parallel linkage B. Namely, the front arm 16 is always kept constant position such as vertical without regard to the up-down movement of the second parallel linkage B.

Figure 2:
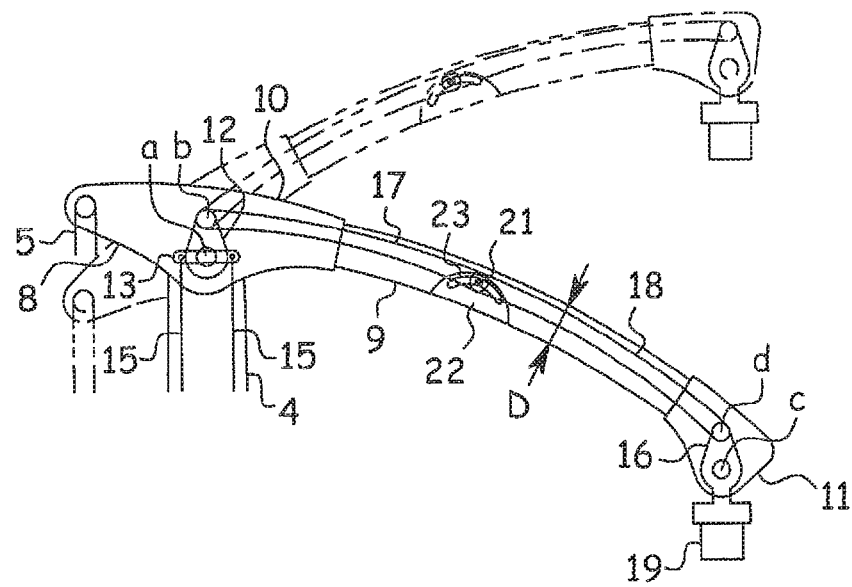
FIG. 2 is a side view illustrating upward and downward movements of upper and lower arms of a parallel linkage formed in the medical stand apparatus.
Figure 4:
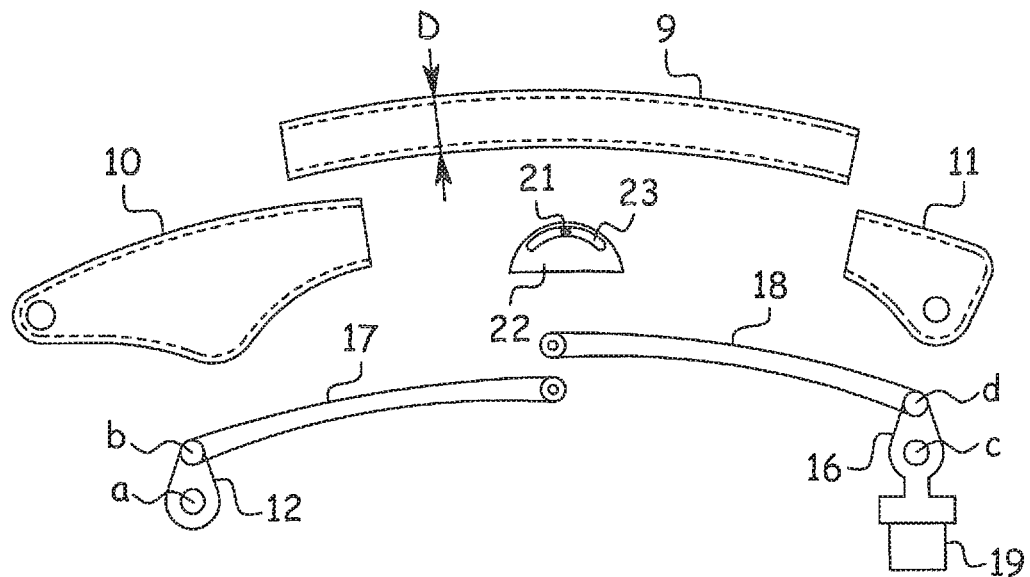
FIG. 4 is an exploded view illustrating the upper and lower arms of the parallel linkage.
Figure 5:
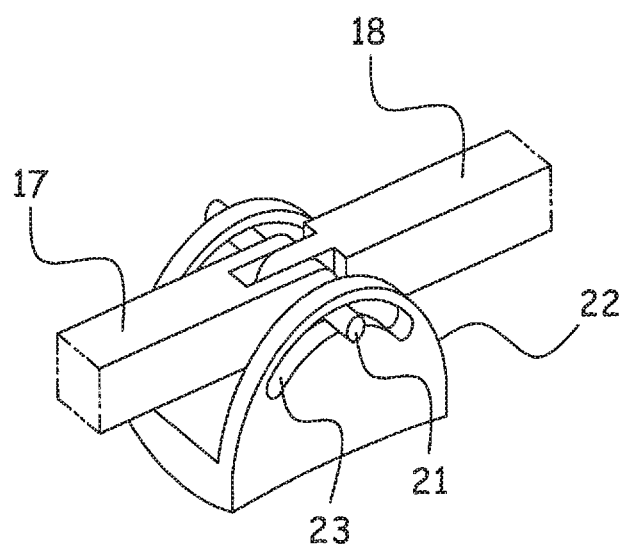
FIG. 5 is a perspective view illustrating a connection between upper arm sections that form the upper arm of the parallel linkage.
Figure 6:
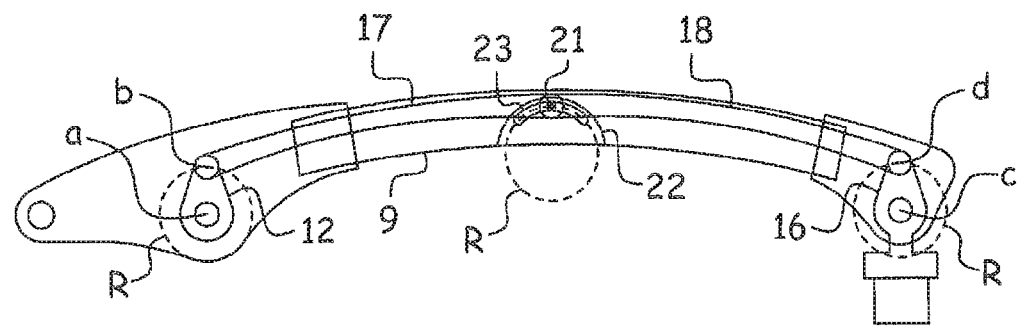
FIG. 6 is a side view illustrating the upper and lower arms of the parallel linkage.
Figure 7:
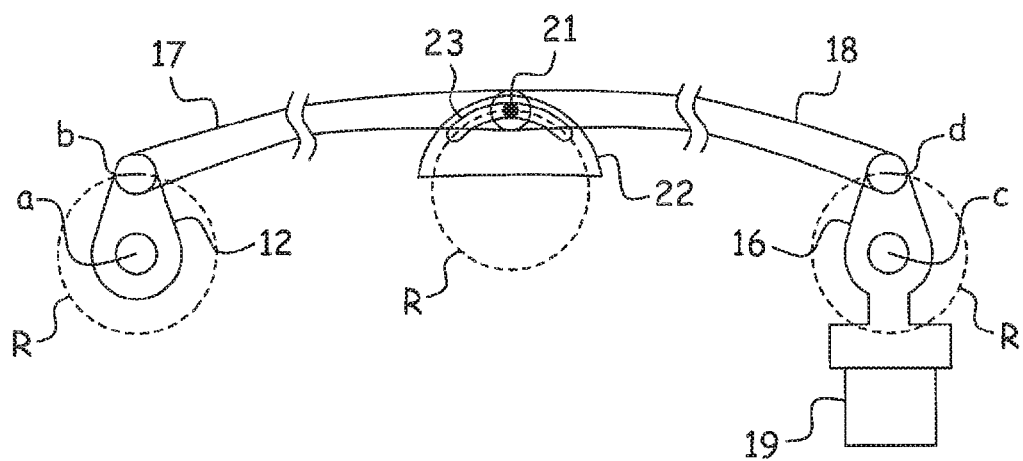
FIG. 7 is an enlarged side view illustrating the upper arm of the parallel linkage.

Generally, the part where the upper arm sections 17 and 18 are connected to each other needs a rotational arm (the common vertical link VC-21) having the same length as the base arm 12, as well as a rotational shaft at the virtual center VC. Instead of such rotational arm and shaft, the embodiment employs the small bracket 22 to provide the same function as that provided by the rotary arm and shaft. With the use of the bracket 22, the embodiment is able to reduce the diameter D of the lower arm 9 as illustrated in FIGS. 2 and 4. Reducing the diameter D of the lower arm 9 results in reducing the weight thereof and clearing sight under the same.

According to the embodiment, the lower arm 9 is cylindrical to accommodate the upper arm 17-18 therein so that only the lower arm 9 is visible from the outside. As a result, the drape P can tightly be fastened to the lower arm 9 with the bands 20 thereby preventing the drape P from sagging to block the sight of an observer.

According to the embodiment, the upper arm 17-18 is halved into the upper arm sections 17 and 18. The upper arm 17-18 may be divided into three sections or more depending on the curvature of the lower arm 9.

According to the embodiment, the arc groove 23 formed on the bracket 22 is open. The arc groove 23 is not necessarily open if it is able to properly guide the connection shaft 21. The bracket 22 and arc groove 23 may be integrally formed with the lower arm 9. Namely, part of the lower arm 9 may be used as the bracket 22 and on which the arc groove 23 is formed.

According to the embodiment, the third parallel linkage C for maintaining the base arm 12 horizontal is formed inside the front arm 4. Such a parallel linkage to keep the base arm 12 horizontal may be formed outside the front arm 4.

In consequence, the present invention employ the cylindrical lower arm to accommodate the upper arm therein so that only the lower arm is visible from the outside, thereby allowing a drape to be tightly fastened to the lower arm.

Another aspect of the present invention divide the upper arm accommodated in the lower arm into a plurality of upper arm sections, thereby reducing the diameter of the lower arm even when the upper and lower arms are curved. The upper arm sections are connected to each other with a connection shaft that is guided along an arc locus of the arc groove of the bracket. This arc locus is equal to each of arc loci along which the upper ends of the base and front arms, i.e., the left and right ends of the upper arm move, respectively, thereby securing the function of the parallel linkage formed with the upper and lower arms.

Furthermore, the present invention arranges the base arm on another parallel linkage that is tiltable in front and rear directions, thereby allowing the parallel linkage formed with the upper and lower arms to move in the front and rear directions.

This patent application claims the benefit of priority under 35 USC 119 (a) to Japanese Patent Application No. 2015-060495 filed on Mar. 24, 2015 whose disclosed contents are cited herein.

What is claimed is:

1. A medical stand apparatus comprising:
   a vertical base arm arranged on the apparatus;
   a vertical front arm including a medical unit disposed at lower part of the front arm;
   an upper arm that is connected to an upper end of the base arm and to an upper end of the front arm; and
   a lower arm that is connected to a lower end of the base arm and to a lower end of the front arm such that the base arm, the front arm, the upper arm, and the lower arm together define a parallel linkage that allows the front arm to move upward and downward with respect to the base arm, wherein
   the upper and lower arms are arranged parallel with each other, and
   the lower arm is a cylindrical member that accommodates the upper arm therein.

2. The medical stand apparatus of claim 1, wherein
   the upper and lower arms are curved, the upper arm is divided into a plurality of upper arm sections, and adjacent ends of the upper arm sections are connected to each other with a horizontal connection shaft so that the connected upper arm sections are turnable around the connection shaft, and
   the lower arm includes a bracket that is fixed to the lower arm inside the lower arm and the bracket has an arc groove that guides the connection shaft, wherein a curvature of the arc groove is equal to that of each of arcs along which the upper ends of the base and front arms move around the lower ends thereof, respectively.

3. The medical stand apparatus of claim 1, wherein
   the base arm is arranged at an upper part of a second parallel linkage of the apparatus, the second parallel linkage being tiltable frontward and rearward.

4. The medical stand apparatus of claim 1, wherein
   the lower arm includes a plurality of hollow members that respectively close ends of the lower arm.

5. A medical stand apparatus comprising:
   a base arm arranged on the apparatus and having a first end to which a first end of a lower arm is rotatably connected;
   an arc groove mechanism having a predetermined length of radius around a virtual center that is positionally fixed to an intermediate part of the lower arm;
   a first sub-link having a first end that is rotatably connected through a shaft to a second end of the base arm, the second end of the base arm being distanced from the first end thereof by the predetermined length, a second end of the first sub-link being movably supported in an arc groove of the arc groove mechanism, the first sub-link, lower arm, and base arm serving as link elements of a first horizontal parallel sub-linkage;
   a second sub-link, a first end thereof being connected to the second end of the first sub-link and movably supported in the arc groove; and
   a vertical sub-link, a second end thereof is connected through a shaft to a second end of the second sub-link, a first end of the vertical sub-link being distanced from the second end of the vertical sub-link by the predetermined length and being connected to a second end of the lower arm, the vertical sub-link supporting a load, and the second sub-link, lower arm, and vertical sub-link serving as link elements of a second horizontal parallel sub-linkage, wherein the first and second horizontal parallel sub-linkages allow the vertical sub-link to move upward and downward with respect to the base arm.

6. The medical stand apparatus of claim 5, wherein the lower arm is cylindrical for accommodating the first and second sub-links therein.

\* \* \* \* \*